(12) United States Patent
Brehm

(10) Patent No.: US 9,291,305 B2
(45) Date of Patent: Mar. 22, 2016

(54) HOLDER FOR A SHELF

(71) Applicant: Fresenius Medical Care Deutschland GmbH, Bad Homburg (DE)

(72) Inventor: Winfried Brehm, Hofheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 162 days.

(21) Appl. No.: 13/740,588

(22) Filed: Jan. 14, 2013

(65) Prior Publication Data

US 2013/0193282 A1     Aug. 1, 2013

Related U.S. Application Data

(60) Provisional application No. 61/585,841, filed on Jan. 12, 2012.

(30) Foreign Application Priority Data

Jan. 12, 2012   (DE) .......................... 10 2012 000 410

(51) Int. Cl.
*F16M 13/02* (2006.01)
*A61B 19/02* (2006.01)
*A61M 5/14* (2006.01)
(Continued)

(52) U.S. Cl.
CPC .......... *F16M 13/022* (2013.01); *A61B 19/0256* (2013.01); *A61B 19/0271* (2013.01); *A61M 5/1415* (2013.01); *A61B 2019/267* (2013.01); *A61M 1/16* (2013.01); *A61M 2209/082* (2013.01)

(58) Field of Classification Search
CPC .... A47B 96/063; A47B 96/061; A47B 57/42; A47B 5/02; A61M 5/1415; A61G 12/008; A47F 5/04; A47F 5/05; A47F 5/06; F16M 11/04; F16M 11/08; F16M 13/02; F16M 13/022; A61B 19/0256; A61B 19/0271; A61B 2019/267
USPC .......... 248/125.7, 124.1, 227.3, 290.1, 230.7, 248/230.1, 219.3, 218.4, 297.51, 211, 248/227.1, 235, 246, 250, 219.4, 125.1, 248/125.9, 282.1, 283.1, 312.1; 108/152, 108/50.12, 42, 97–98, 151; D24/128; 211/107, 131.1, 144, 205; D6/681.3; 604/5.04, 6.09; 403/145, 147
See application file for complete search history.

(56) References Cited

U.S. PATENT DOCUMENTS

| 783,837 A * | 2/1905 | Johnston ................... 248/216.1 |
| 1,261,755 A * | 4/1918 | Beyle ....................... 248/125.8 |

(Continued)

FOREIGN PATENT DOCUMENTS

DE     196 31 877     2/1998

*Primary Examiner* — Ingrid M Weinhold
(74) *Attorney, Agent, or Firm* — Jacobson Holman, PLLC

(57) ABSTRACT

A holder for mounting a shelf on an infusion stand of a medical device, for example, a dialysis machine, has a surface element that is connectable to the infusion stand, a shelf carrier that is integral with an outer edge of the surface element, and a holder supporting element. With this holder, a shelf surface for utilitarian objects on the dialysis machine is made available to the user. A shelf which is to be fastened on the infusion stand is necessary in particular with dialysis machines whose display screen in not integrated into the machine housing but instead is attached to the infusion stand. The surface of the machine in this case can no longer be used as a shelf surface. The holder can be mounted and removed easily without the assistance of tools.

15 Claims, 3 Drawing Sheets

(51) Int. Cl.
*A61M 1/16* (2006.01)
*A61B 19/00* (2006.01)

(56) References Cited

U.S. PATENT DOCUMENTS

| | | | | |
|---|---|---|---|---|
| 1,799,079 | A * | 3/1931 | Bemis | 248/146 |
| 2,367,256 | A * | 1/1945 | Atkins | 248/210 |
| 2,481,604 | A * | 9/1949 | Lorenzen | 108/152 |
| 2,765,999 | A * | 10/1956 | Baker | 248/124.1 |
| 3,322,381 | A * | 5/1967 | Bubb | 248/121 |
| 3,370,820 | A * | 2/1968 | Liss et al. | 248/312.1 |
| D301,977 | S * | 7/1989 | Moody et al. | D8/373 |
| 4,878,642 | A | 11/1989 | Kirby, Jr. | |
| 5,114,023 | A * | 5/1992 | Lavin | 211/107 |
| 5,169,106 | A | 12/1992 | Rasmussen | |
| D346,655 | S * | 5/1994 | Harris | D24/128 |
| 5,337,992 | A * | 8/1994 | Pryor et al. | 248/125.1 |
| 5,356,107 | A | 10/1994 | Sinohuiz | |
| 5,395,081 | A * | 3/1995 | Vollink | 248/218.4 |
| 5,644,993 | A * | 7/1997 | Dohnalik | 108/108 |
| 5,655,741 | A * | 8/1997 | Watkins | 248/289.11 |
| D405,682 | S * | 2/1999 | Suher | D8/370 |
| 6,250,482 | B1 * | 6/2001 | Want et al. | 211/181.1 |
| 6,409,131 | B1 | 6/2002 | Bentley et al. | |
| 6,688,238 | B1 * | 2/2004 | Alexiou | 108/42 |
| 7,258,197 | B1 * | 8/2007 | Wicks | 182/82 |
| 7,503,265 | B1 * | 3/2009 | Hammond | 108/50.12 |
| 7,935,250 | B2 * | 5/2011 | Castellano et al. | 210/143 |
| 7,967,137 | B2 | 6/2011 | Fulbrook et al. | |
| 8,015,929 | B2 * | 9/2011 | Tyner | 108/134 |
| 8,348,072 | B2 * | 1/2013 | Whitehall et al. | 211/196 |
| D692,132 | S * | 10/2013 | Damron | D24/128 |
| 2003/0121873 | A1 * | 7/2003 | Lippman et al. | 211/163 |
| 2004/0064080 | A1 * | 4/2004 | Cruz et al. | 604/5.04 |
| 2005/0016044 | A1 | 1/2005 | Kubicek et al. | |
| 2007/0267551 | A1 | 11/2007 | Townsend | |
| 2009/0284108 | A1 * | 11/2009 | Castellano et al. | 312/209 |
| 2009/0294604 | A1 * | 12/2009 | Sunderland | 248/124.1 |
| 2009/0301927 | A1 * | 12/2009 | Fvlbrook et al. | 206/564 |
| 2014/0027589 | A1 * | 1/2014 | Durgin | 248/218.4 |

* cited by examiner

HOLDER FOR A SHELF

BACKGROUND OF THE INVENTION

1. Field of Invention

The invention relates to a holder for mounting an object, e.g., a tray-type shelf, on the infusion stand of a medical device such as a dialysis machine. This provides an area for depositing utilitarian objects for the nursing and service personnel at the treatment station.

2. Description of the Prior Art

Devices which allow a variety of objects to be placed on and stored directly on an infusion stand are known in the state of the art.

US 2007/0267551 describes a holder for an infusion stand, which serves to hold a patient's personal items, so the patient can have the items with him continuously along with the infusion stand. This holder is attached to the infusion stand by a screw clamp. Such screw clamps consist of several parts and are very difficult to clean because of their design. Hygiene plays a major role in a medical environment, and smooth surfaces are preferred to facilitate cleaning and disinfection.

US 2005/0016044 describes the fastening of objects, such as frames, on an infusion stand with the help of a flexible metal cable, which is wound around the stand. Installation and dismantling both tend to be complicated jobs.

US 2009/0294604 describes fastening means which can be attached in a one-handed operation, their fastening onto the stand being accomplished by friction. One disadvantage of this device is that it can easily slip in the absence of a load. Special clamping jaws must therefore be provided in the infusion stand to hold the holders in the desired position when friction is not sufficient to secure them in the absence of a weight load.

U.S. Pat. No. 7,967,137 describes a shelf that can be clamped on a holder on an infusion stand. This holder is attached to the infusion stand by means of a screw clamp.

Statement of Problem

In treating patients, in particular in dialysis therapy, physicians and nurses require different utilitarian materials directly at the treatment station, for example, such materials as disinfectants, adhesive tape, access cannulas, etc. These are usually stored on the surface of the dialysis machine, for example. With some dialysis machines, the display screen, which may serve as both display means and as input means is not integrated into the machine housing. For example, the display screen may be attached to the surface of the machine by means of a movable carrying arm. This attachment may also be used for anchoring and infusion stand. The user can therefore move the display screen into different positions, which allow the user to read the information conveniently and possibly to enter treatment data, depending on the local conditions. With this design, however, the surface of the machine housing is no longer suitable for use as a shelf surface.

Furthermore, a few utility materials are needed by the nursing personnel at each treatment station. These materials must then either be stored at each treatment station, which is a disadvantage because of the prevailing lack of space, or as an alternative, it must be transported on a tray by the nursing personnel from one treatment station to the next.

The object of the present invention is to make available to the physician or nursing personnel a shelf surface directly on the treatment machine.

According to the teaching of the invention, this object is achieved by a holder having the features described herein, the use of the holder, and a dialysis machine that incorporates the holder. Advantageous embodiments of the invention are also described herein.

SUMMARY OF THE INVENTION

The invention relates to a holder for detachably attaching a shelf which can be attached to an infusion stand of a medical device, in particular a dialysis machine. The holder consists of a surface to which at least one carrier is attached to the outer edge in one piece. A shelf of the tray type, for example, may be detachably attached to this carrier. In addition, a supporting means in the form of a curved element is provided on the outer edge of the surface and perpendicular to it. The surface also has a central recess, which serves to hold the infusion stand. To guide the infusion stand into this central recess, a notch is provided from the outer edge of the surface to the central recess.

In a special embodiment, the area is designed to be largely circular. To mount the holder on the infusion on the infusion stand, the infusion stand must inserted into the central recess. The notch provided for this purpose is preferably designed with a curve. A hook which forms an especially secure fastening is formed by the bending.

The display screen of the medical device may be attached to a carrying arm. A movable joint may be located between the display screen and the carrying arm. The carrying arm itself may also be designed in two parts, wherein the two parts are linked together by a joint. The carrying arm may be mounted on the machine surface with a fastener which may be designed to be cylindrical or conical, for example. The carrying arm may be rotatable about the fastening so that the user can orient the screen toward different sides of the machine. The user gains additional degrees of freedom with respect to the orientation of the screen through the two joints in the carrying arm.

The display screen may serve to display information for the user or may also be used as a touchscreen for input of treatment data or treatment parameters. In a preferred embodiment, the holder may be designed so that the largely circular area and the supporting means fit together in a form-fitting manner with a fastener for the carrying arm of the display screen on the machine surface. The a curved in the supporting means may preferably extend over an angle between 110° and 180°.

In a preferred embodiment, the carrier for the shelf attached to the surface consists of at least two holding means. An upper holding means may be embodied as a hook in which the edge of the shelf can be suspended. A lower holding means may be embodied as a supporting surface which supports the shelf from underneath.

The holder can be rotated about the infusion stand. The holder may be designed so that it rotates on rotation of the carrying arm for the display screen around the infusion stand based on the frictional resistance between the fastening of the carrying arm on the machine surface and the holder at the same angle amount. The tray-type shelf is thus rotated around the infusion stand in parallel with the display screen. The position of the display screen and the tray-type shelf in relation to one another remains the same. The carrying arm or the holder may also be rotated independently of one another by manual fixation of the carrying arm, the screen, the holder or the tray-type shelf. The position of the screen and the tray-type shelf can thus be adjusted in relation to one another.

A stop for the carrying arm beyond which rotation is impossible is formed by the vertical edge of the supporting means. This largely prevents collisions of the screen and the tray-type shelf.

Due to the notch, which is designed to be curved from the edge of the surface to the central recess, the holder is to be attached to the infusion stand by hook engagement and unlocked.

The holder is preferably made of plastic, e.g., PET or ABS. In an alternative embodiment, however, it may also be made of metal.

To avoid damage due to abrasion, the holder may have a glass strip on the supporting means.

The central recess may be provided with a reinforcing rib to reduce the stress.

The invention also relates to the use of the holder as described herein, for fastening a shelf surface on the infusion stand of a medical device, in particular a dialysis machine.

The invention also relates to a dialysis machine having a fastener for a carrying arm with a display screen and an infusion stand on which a holder as described herein, with a shelf, is attached.

BRIEF DESCRIPTION OF THE DRAWINGS

Additional details and advantages of the invention are described in greater detail on the basis of the exemplary embodiments shown in the drawings, in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
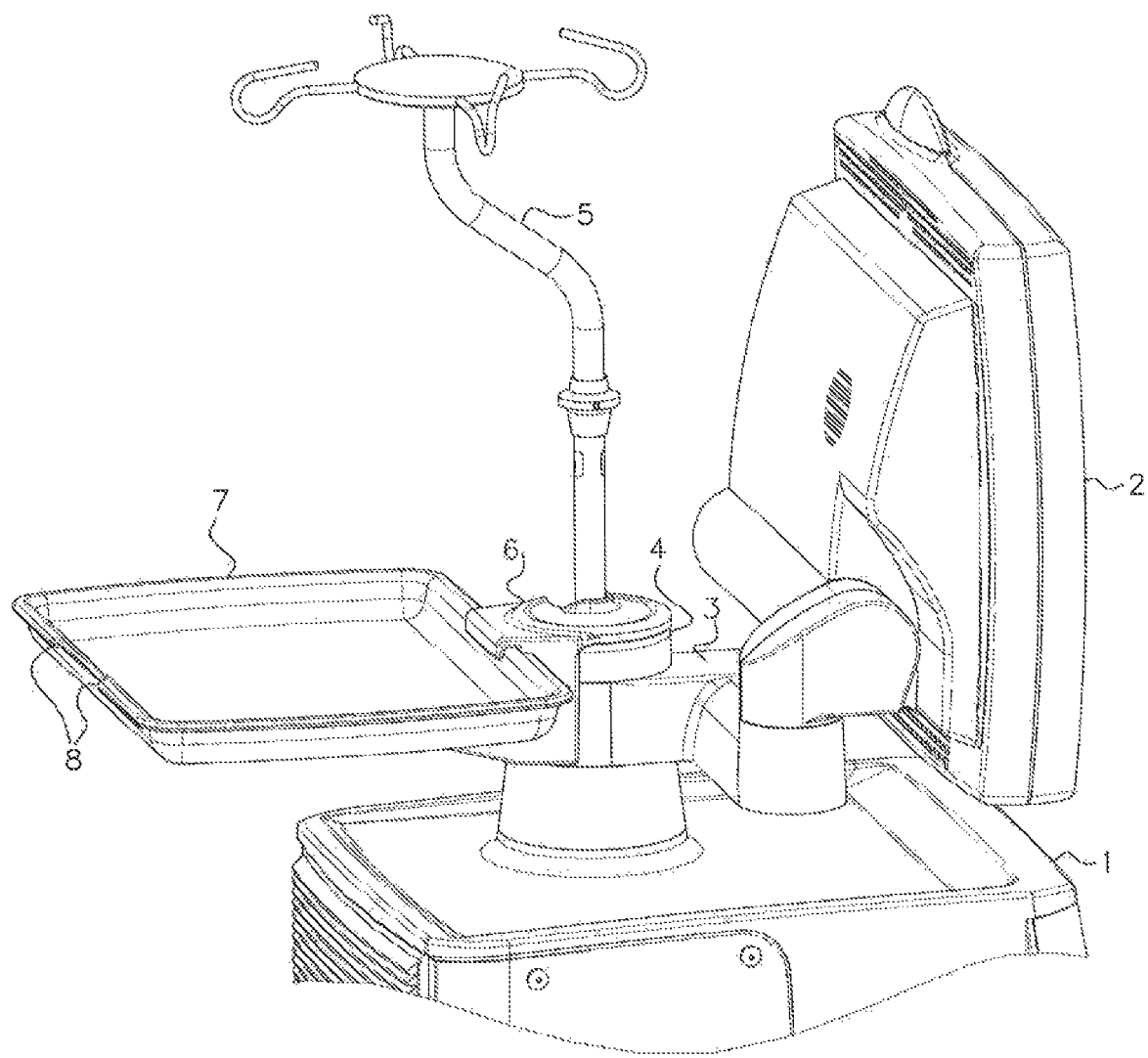
FIG. 1: shows a perspective view of an inventive holder with a shelf and a display screen on an infusion stand of a medical device.

FIG. 1 shows a dialysis machine 1 with an infusion stand 5 on the housing surface, as seen obliquely from the rear. The infusion stand 5 is mounted on a fastening means (i.e., a fastening element) 4 for a carrying arm 3 with a display screen 2. The fastening means 4 may be rotated about the central axis. A holder 6 according to the invention is suspended by a hook on the infusion stand 5 by means of the fastening means 4. A tray-type shelf 7 is attached to the holder 6. The tray-type shelf consists of a rectangular area with a largely vertical edge connected thereto. The edge has a recess 8 on at least one side, limiting the lateral displacement of tray-type shelf 7 in the holder 6. The embodiment shown in FIG. 1 has the recess 8 on two opposite sides, so that a recess engages with the holder.

The holder 6 and the fastening means 4 for the carrying arm 3 fit together in a form-fitting manner. The frictional resistance between the holder 6 and the fastening means 4 has the effect that when the user rotates the screen 2 with the carrying arm 3 about the infusion stand 5, the holder also rotates with it. If the screen 2 or the tray-type shelf 7 is secured in place, then both may also be rotated about the infusion stand independently of one another.

Figure 2:
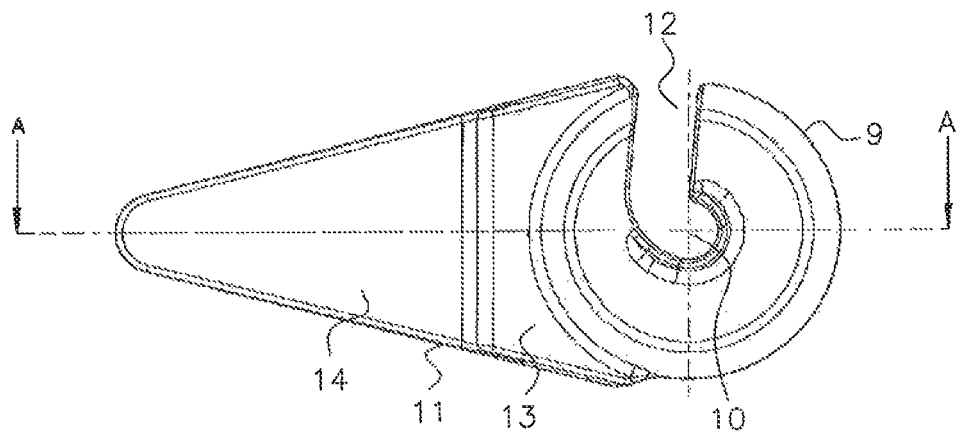
FIG. 2: shows a top view of the holder with a circular area and carrier.

The holder 6 is shown in a view from above in FIG. 2. The holder 6 has a largely circular surface (i.e., a surface element) 9 with a central recess 10. A curved notch 12 leads from the outer edge of the surface 9 to this central recess 10. By guiding the infusion stand 5 through this curved notch 12 to the central recess 10, the holder can be suspended by hook in the infusion stand. This can be accomplished without the help of tools and by using a single hand.

The axis of symmetry of the notch 12 and the axis of symmetry of the carrier 11 are approximately perpendicular to one another. This ensures that in a weight loading of the holder 6 and the tray-type shelf 7, the infusion stand cannot slip out of the holder 6 because the main load lies in the axis of symmetry of the carrier 11. The bending of the notch prevents the holder from being released from the infusion stand by tilting even in the event the tray is put under load at one end.

The carrier 11 is connected to the surface 9. The carrier consists of an upper holding means 13, which is embodied as a hook gripping downward and a lower holding means 14, which is embodied here as a wedge-shaped supporting surface. However, other forms which produce a stable fastening of the tray-type shelf are also conceivable.

Figure 3:
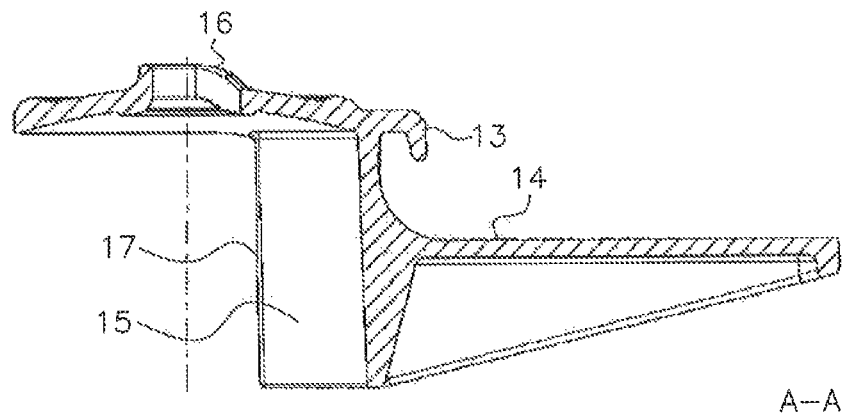
FIG. 3: shows a cross section through the holder.

FIG. 3 shows a cross section through the holder with the surface 9 and largely perpendicular to the surface 9 a supporting means (i.e., a holder supporting element) 15 which is in the form of a curved element. The supporting means 15 are embodied so that together with the surface 9 it fits with the fastening means 4 of the carrying arm 3 largely in a form-fitting manner. The vertical delimitation of the supporting means 15 forms a stop 17 for the carrying arm 3. Collisions between the tray-type shelf 7 and the display screen 2 are largely prevented by rotating the tray-type shelf 7 or the screen 2 about the infusion stand 5. The two holding means 13 and 14 of the carrier 11 are designed in one piece on the surface 9 and the supporting means 15. Holding means 13 is in the form of a hook directed downward. Holding means 14 forms a horizontal supporting surface. By tilting it slightly, the tray-type shelf 7 can be clamped in the holder and/or removed from it. This may also be accomplished with a tray-type shelf holding some items, for example.

The surface 9, which serves as the supporting surface on the fastening means 4, also has a reinforcing rib 16 around the central recess, counteracting deformation of the holder due to stresses in loading the tray-type shelf 7.

The holder 6 consisting of the surface 9, the supporting means 15 and the carrier 11 with the holding means 13 and 14 is designed in one piece. It may be made of plastic, for example, and manufactured by injection molding. The tray-type shelf 7 is detachably connectable to the holder 6. The holder 6 is detachably mounted on the infusion stand 5. Fastening and removal of the holder 6 and the tray-type shelf 7 are accomplished very easily without the assistance of tools due to the shape of the holder. The dialysis machine may be equipped with this holder subsequently. A holder can easily be switched from one dialysis machine to another as needed. Since the tray-type shelf is very easily mounted and removed, the nurse may also place his disposable items on a tray, for example, and carry them from one treatment station to the next and attach them there to the infusion stand if the latter is provided with a holder 6.

Figure 4:
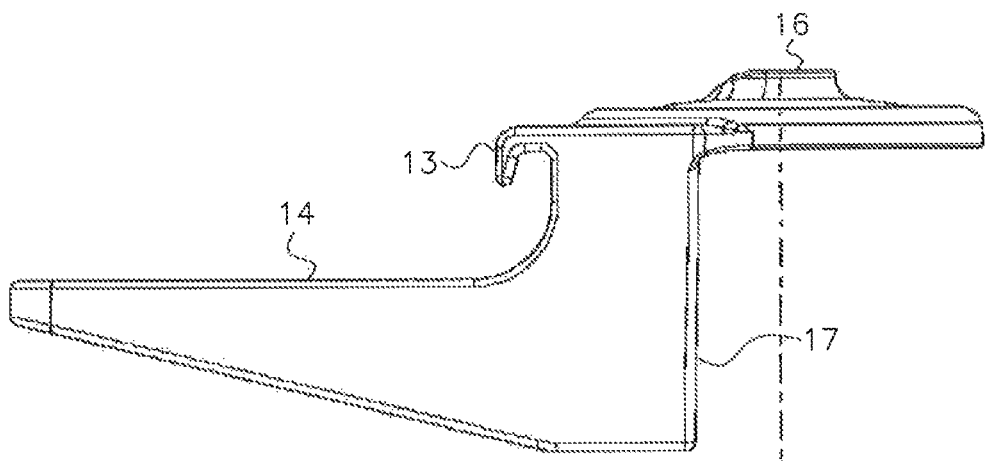
FIG. 4: shows side view of the holder.
Figure 5:
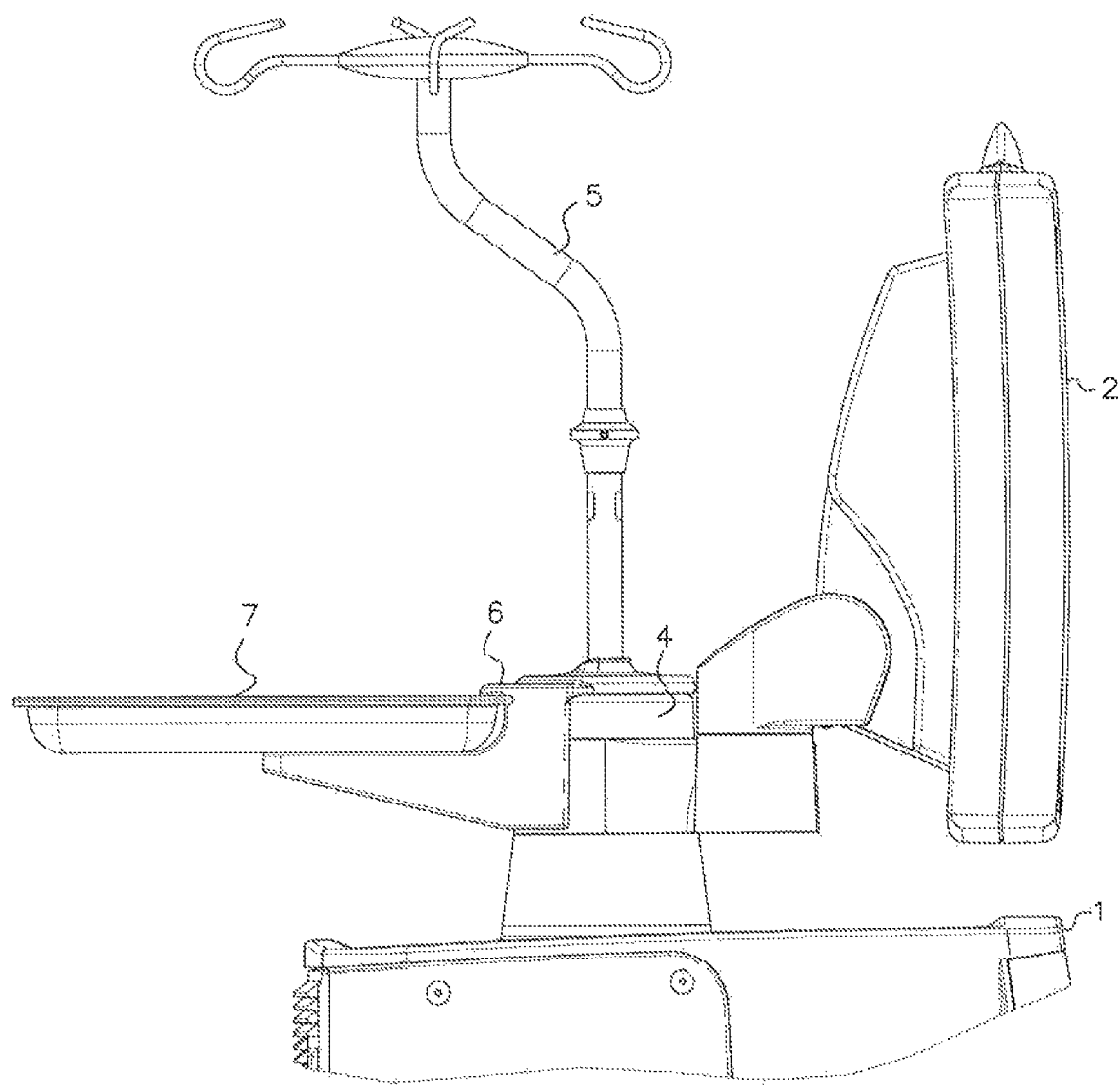
FIG. 5 is a side view of the inventive holder shown in FIG. 1.

FIG. 4 shows a side view of the holder 6.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A holder for the releasable connection of a shelf on an infusion stand of a medical device that has a displays screen carrying arm and an associated fastening element, said holder comprising:
a surface element that is connectable to the infusion stand;
a shelf carrier that is integral with an outer edge of the surface element; and
a holder supporting element configured as a curved element extending from the outer edge of the surface element, the holder supporting element being substantially perpendicular to the surface element,
the surface element including therein a central recess, and a notch that extends from the out edge of the surface element to the central recess, with the notch being configured to guide the infusion stand into the central recess,
with the surface element and the holder supporting element fitting together in a form-fitting manner with the fastening element of the medical device,
wherein the holder is adapted to rotate together with the carrying arm, the holder being rotatable by a same angle amount as rotation of the carrying arm about a central axis of the fastening element due to frictional resistance between the fastening element of the carrying arm and the holder.

2. The holder according to claim 1, wherein the surface element is substantially circular.

3. The holder according to claim 1, wherein the notch has a curved shape.

4. The holder according to claim 1, wherein the curved element of the holder supporting element extends over an angle of between 110° and 180°.

5. The holder according to claim 1, wherein the shelf carrier includes a first holding element and a second holding element.

6. The holder according to claim 5, wherein the first holding element is a hook and the second holding element is designed as a supporting surface for the shelf.

7. The holder according to claim 1, wherein the holder is rotatable about the infusion stand.

8. The holder according to claim 1, wherein by manual fixation of the carrying arm, the holder is independently rotatable about the infusion stand.

9. The holder according to claim 1, wherein the holder supporting element includes a stop for the carrying arm, beyond which rotation of the carrying arm is impossible.

10. The holder according to claim 1, wherein the holder is suspendable on the infusion stand via the notch.

11. The holder according to claim 1, wherein the holder has a material of construction that is a plastic.

12. The holder according to claim 1, wherein the medical device is a dialysis machine.

13. The holder according to claim 1, wherein the shelf carrier is configured to releasably hold a detachable shelf.

14. The holder according to claim 13, wherein the detachable shelf is a tray.

15. A dialysis machine comprising:
an infusion stand on a surface of the dialysis machine;
a carrying arm for a display screen;
a holder for releasable connection of a shelf to the infusion stand; and
a fastening element that supports the carrying arm and the holder,
the holder including
a surface element that is connectable to the infusion stand,
a shelf carrier that is integral with an outer edge of the surface element, and
a holder supporting element configured as the curved element extending from the outer edge of the surface element, the holder supporting element being substantially perpendicular to the surface element,
the surface element including therein a central recess, and a notch that extends from the outer edge of the surface element to the central recess, with the notch being configured to guide the infusion stand into the central recess,
with the surface element and the holder supporting element fitting together in a form-fitting manner with the fastening element,
wherein the holder is adapted to rotate together with the carrying arm, the holder being rotatable by a same angle amount as rotation of the carrying arm about a central axis of the fastening element due to frictional resistance between the fastening element of the carrying arm and the holder.

* * * * *